US008790269B2

(12) United States Patent
Xu et al.

(10) Patent No.: US 8,790,269 B2
(45) Date of Patent: Jul. 29, 2014

(54) MONITORING RESPIRATION WITH A THERMAL IMAGING SYSTEM

(75) Inventors: Beilei Xu, Penfield, NY (US); Lalit Keshav Mestha, Fairport, NY (US); Graham Pennington, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 372 days.

(21) Appl. No.: 13/103,406

(22) Filed: May 9, 2011

(65) Prior Publication Data

US 2012/0289850 A1 Nov. 15, 2012

(51) Int. Cl.
*A61B 5/08* (2006.01)

(52) U.S. Cl.
USPC .......................................... 600/529; 600/534

(58) Field of Classification Search
USPC .................................................. 600/529–538
See application file for complete search history.

(56) References Cited

U.S. PATENT DOCUMENTS

| | | | |
|---|---|---|---|
| 5,010,890 A * | 4/1991 | Pfohl et al. ..................... 600/528 |
| 5,107,845 A | 4/1992 | Guern et al. | |
| 5,800,360 A | 9/1998 | Kisner et al. | |
| 6,920,236 B2 | 7/2005 | Prokoski | |
| 6,958,809 B2 | 10/2005 | Sterling et al. | |
| 6,989,891 B2 | 1/2006 | Braig et al. | |
| 7,050,157 B2 | 5/2006 | Braig et al. | |
| 7,061,593 B2 | 6/2006 | Braig et al. | |
| 7,436,510 B2 | 10/2008 | Grun et al. | |
| 7,480,032 B2 | 1/2009 | Braig et al. | |
| 7,570,979 B2 | 8/2009 | Cooper | |
| 7,729,750 B2 | 6/2010 | Tromberg et al. | |
| 7,738,085 B2 | 6/2010 | Braig et al. | |
| 7,760,354 B2 | 7/2010 | Grun et al. | |
| 7,872,734 B2 | 1/2011 | Braig et al. | |
| 7,896,498 B2 | 3/2011 | Munger et al. | |
| 7,899,764 B2 | 3/2011 | Martin et al. | |
| 2002/0008758 A1 * | 1/2002 | Broemmelsiek et al. ..... 348/143 |
| 2009/0275808 A1 | 11/2009 | DiMaio et al. | |
| 2009/0318815 A1 | 12/2009 | Barnes et al. | |

OTHER PUBLICATIONS

Takeo Kanade, Computer Recognition of Human Faces, 1977, Birkhäuser Verlag, Basel und Stuttgart.*
Moore, David, "A Real-World System for Human Motion Detection and Tracking", Final Thesis, California Institute of Technology, (2003).

(Continued)

*Primary Examiner* — Michael Kahelin
*Assistant Examiner* — Yunqing Wang
(74) *Attorney, Agent, or Firm* — Philip E. Blair; Fleit Gibbons Gutman Bongini & Bianco P.L.

(57) ABSTRACT

What is disclosed is a system and method for monitoring respiration of a subject or subject of interest using a thermal imaging system with single or multiple spectral bands set to a temperature range of a facial region of that person. Temperatures of extremities of the head and face are used to locate facial features in the captured thermal images, i.e., nose and mouth, which are associated with respiration. The RGB signals obtained from the camera are plotted to obtain a respiration pattern. From the respiration pattern, a rate of respiration is obtained. The system includes display and communication interfaces wherein alerts can be activated if the respiration rate falls outside a level of acceptability. The teachings hereof find their uses in an array of devices such as, for example, devices which monitor the respiration of an infant to signal the onset of a respiratory problem or failure.

25 Claims, 7 Drawing Sheets

(56) References Cited

OTHER PUBLICATIONS

Wang, et al., "Intelligent Multimodal and Hyperspectral Sensing for Real-Time Moving Target Tracking", Applied Imagery Pattern Recognition Workshop (AIPR), pp. 1-8, (2008).

Al-Khalidi, et al., "Tracking Human Face Features in Thermal Images for Respiration Monitoring", IEEE/ACS Int'l Conf. on Computer Systems and Applications (AICCSA), Hammamet, Tunisia, (May 16-19, 2010).

Fei, et al., Analysis of Breathing Air Flow Patterns in Thermal Imaging, Proceedings of the 28th IEEE EMBS Annual International Conference, New York City, USA, pp. 946-952, (Aug. 30-Sep. 3, 2006).

Aoki, et al., "Study on Respiration Monitoring Method Using Near-infrared Multiple Slit-lights Projection", IEEE International Symposium on Micro-NanoMechatronics and Human Science, pp. 291-296, (Nov. 7-9, 2005), ISBN: 0-7803-9482-8.

Eveland, et al., "Tracking Human Faces in Infrared Video", Image and Vision Computing, vol. 21, pp. 579-590 (2003).

Aoki, et al., Non-contact and Unrestrained Respiration Monitoring System for Sleeping Person Using Near-infrared Bright Spots Matrix Irradiation, IEEJ Transactions on Electronics, pp. 1251-1258, vol. 124, No. 6, (Sep. 2004).

Murthy, et al., Non-Contact Monitoring of Breathing Function Using Infrared Imaging, pp. 1-17, Technical Report No. UH-CS-05-09, Apr. 9, 2005.

* cited by examiner

US 8,790,269 B2

MONITORING RESPIRATION WITH A THERMAL IMAGING SYSTEM

TECHNICAL FIELD

The present invention is directed to systems and methods which utilize a thermal camera with single or multiple spectral bands to monitor the respiration function.

BACKGROUND

Methods for monitoring the respiratory function of a person have many applications in medicine, sleep studies, polygraph testing, to name a few. However, such systems have involved the use of wires and electrodes or other physically invasive apparatus which contact the subject and thus interfering with their rest.

In recent years, infrared imaging technology has been applied to this problem as images in the infrared are invariant to ambient light and contain a great deal of data. The use of infrared imaging for measuring a respiratory function is based on the fact that air near the nostril has a temperature that is varying with inhale and exhale. However, problems have arisen with regards to methods for analyzing the captured infrared images or thermal video sequence such as, for instance, determining facial areas associated with respiration and then determining a respiration rate or respiration pattern from the image. Moreover, the infrared images have to be processed in real time on a frame-by-frame basis if the subject's respiratory function is intended to be continuously monitored over a prolonged period of time such as a sleep cycle.

Accordingly, what is needed in this art is a thermal imaging system and method capable of capturing a video sequence of subject(s) of interest, and processing the captured image sequence on a frame-by-frame basis such that their respiratory function can be continuously monitored in a safe, reliable, non-contact, and non-invasive manner without disturbing or disrupting the subject's rest or sleep.

INCORPORATED REFERENCES

The following U.S. patents, U.S. patent applications, and Publications are incorporated herein in their entirety by reference.

"A Real-World System For Human Motion Detection And Tracking", David Moore, Final Thesis, California Institute of Technology, (2003).

"Intelligent Multimodal And Hyperspectral Sensing For Real-Time Moving Target Tracking", Tao Wang, Zhigang Zhu, Applied Imagery Pattern Recognition Workshop (AIPR), pp. 1-8, (2008).

"Tracking Human Face Features In Thermal Images For Respiration Monitoring", F. Q. Al-Khalidi, R. Saatchi, D. Burke, H. Elphick, IEEE/ACS Int'l Conf. on Computer Systems and Applications (AICCSA), Hammamet, Tunisia, (2010).

"Principles of Anatomy and Physiology", Gerard J. Tortora, Bryan H. Derrickson, Wiley; $13^{th}$ Ed. (2011), ISBN-13: 978-0470565100.

"Infrared Thermal Imaging: Fundamentals, Research and Applications", Michael Vollmer, Klaus Peter Möllmann, Wiley-VCH; $1^{st}$ Ed. (2010) ISBN-13: 978-3527407170.

"Analysis of Breathing Air Flow Patterns in Thermal Imaging", Proceedings of the $28^{th}$ IEEE EMBS Annual International Conference, New York City, USA, (Aug. 30-Sep. 3, 2006).

"Study on Respiration Monitoring Method Using Near-infrared Multiple Slit-lights Projection", Hirooki Aoki, Kohji Koshiji, Hidetoshi Nakamura, Yasuhiro Takemura, Masato Nakajima, IEEE International Symposium on Micro-Nano-Mechatronics and Human Science, pp. 291-296, (Nov. 7-9 2005), ISBN: 0-7803-9482-8

BRIEF SUMMARY

What is disclosed is a novel system and method for monitoring respiration of a subject of interest using a thermal imaging system. Temperature differences of extremities of the subject's head and face are identified in the thermal images and used to locate facial features of the subject which are associated with respiration. Once these facial features have been isolated, RGB values of pixels associated with the identified facial features in the image are tracked over time to generate a pattern of respiration. A respiration rate is determined from the respiration pattern. The teachings hereof effectuate the continuous monitoring of a subject's respiration rate in an accurate and reliable manner. Alerts can be activated if the subject's respiration rate falls outside a pre-defined level of acceptability or if anomalies are determined to be present in their respiration pattern. The teachings hereof find their uses in a wide array of products such as, for example, medical devices used to monitor the respiratory function of premature babies in a neonatal intensive care unit (NICU) and homecare products which monitor sleeping infants such that Sudden Infant Death Syndrome (SIDS) can be detected and an alarm signal initiated if the subject's respiratory function falls outside acceptable parameters.

In one example embodiment, the present system and method for monitoring respiration using a thermal imaging system involves the following. First, a video sequence of thermal images of a subject of interest intended to be monitored for respiration are captured using a thermal camera set to a temperature range of a facial region of the subject. Each thermal image comprises a plurality of pixels each having associated values corresponding to a surface temperature of the facial region across the camera's thermal wavelength band. As thermal images of the subject's head and face are received, temperature values of pixels in the image stream are analyzed to determine a location of one or more extremities of the subject's head and face. Once these extremities have been located, either the locational information is retrieved from a database which facilitates the isolation of facial features associated with respiration or the locations of the extremities are directly used to identify an ROI where facial features associated with respiration might be located. The facial features associated with respiration are then analyzed on a frame-by-frame basis. A respiration pattern is then generated by tracking, over time pixel, values received from the camera associated with these facial feature locations. The subject's respiration rate is determined from the respiration pattern. In such a manner, the subject's respiration rate and/or respiration pattern can be continuously monitored. An alarm signal is sent in response to the monitored respiration rate and/or respiration pattern falling outside pre-defined threshold levels.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for capturing a video sequence of a subject of interest and automatically processing those captured thermal images such that the subject's respiratory function can be continuously and safely monitored without any contact sensors on the subject.

Non-Limiting Definitions

A "subject of interest, as used herein, is intended to encompass any living creature which has a facial feature associated with respiration.

Figure 1A:
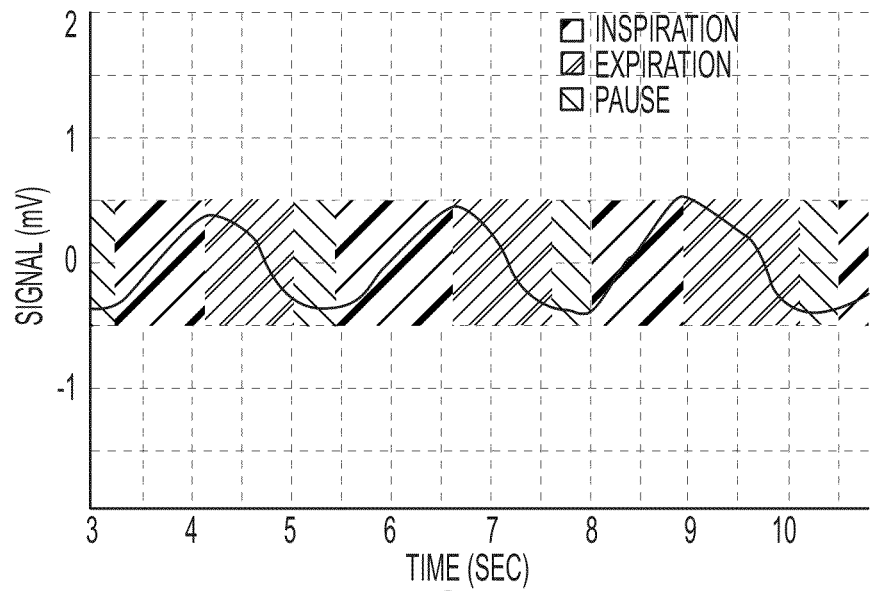
FIG. 1 shows an output from a piezo-respiratory belt transducer showing the three breathing phases during (a) quiet breathing and (b) after exercise.
Figure 1B:
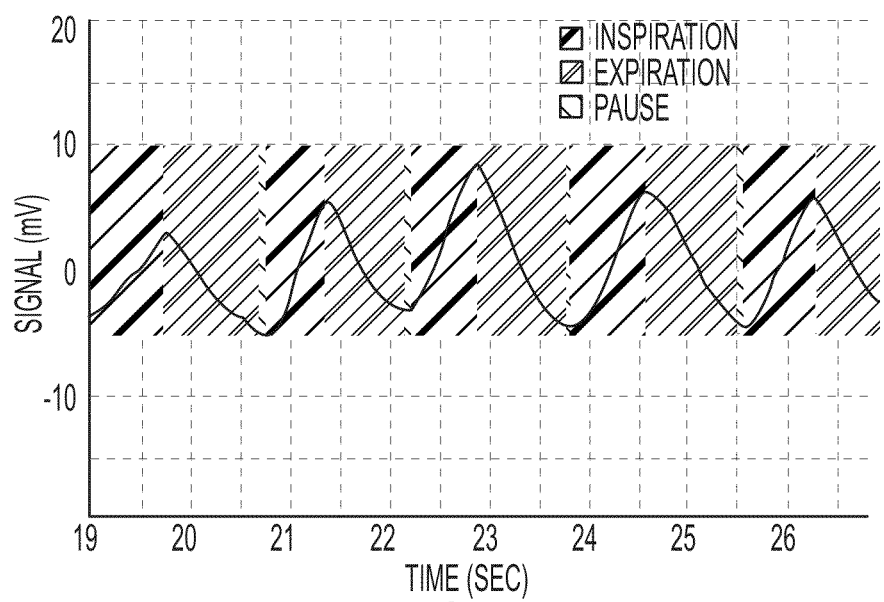

"Respiration", as is normally understood, is a process of inhaling of air into lungs and exhaling air out of the lungs followed by a post-expiratory pause. Inhalation is an active process caused by a negative pressure having been induced in the chest cavity by the contraction of a relatively large muscle (often called the diaphragm) which changes pressure in the lungs by a forcible expansion of the lung's alveolar cells. Exhalation is a passive process where air is expelled from the lungs by the natural elastic recoil of the stretched alveolar cells. The lining of alveolar cells have a surface-active phospholipoprotein complex which causes the lining to naturally contract back to a neutral state once the external force causing the cell to stretch has released. A post-expiratory pause occurs when there is an equalization of pressure between the lungs and the atmosphere. When the subject is at rest, the duration of the post-expiratory pause can be relatively long. The duration of the post-expiratory pause reduces with increased physical activity and may even fall to zero at very high rates of exertion. FIGS. 1(a) and 1(b) show a typical duration of the three phases of breathing during inactivity and after physical exertion.

A "breathing cycle" is the time interval between the beginning of inhalation and the end of the post-expiratory pause. Immediately following the post-expiratory pause is the start of the next breathing cycle.

Figure 2:
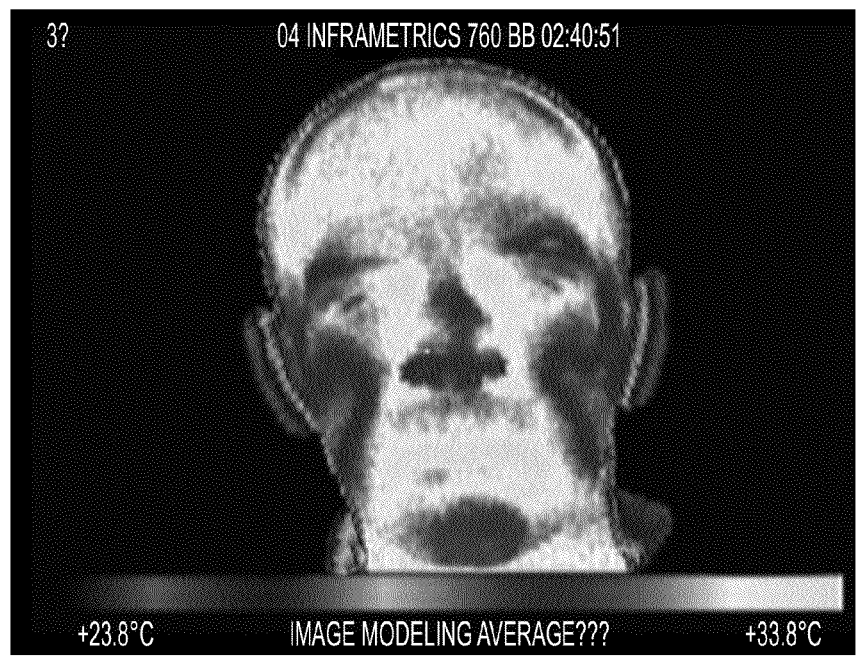
FIG. 2 is an thermal image of the head and face which illustrates pixel temperature differences of various extremities of the subject's head and face.

An "extremity of the head and face" refers to a physical feature of the head and face of the subject of interest which may be isolated in a thermal image as a result of a temperature difference. Head and face extremities can include: ears, tip of the chin, tip of the nose, cheeks, and the like. Extremities of the head and face are used herein to determine a location of the subject's facial feature associated with respiration. In the image of FIG. 2, the ears are used to locate the mouth/nose (facial feature associated with respiration).

A "facial feature associated with respiration" refers to an air passageway through which oxygenated air is received into the lungs during inhalation and carbon-dioxide rich air is expelled out of the lungs during exhalation. Facial features associated with respiration are determined in the thermal images by various pre-defined locational relationships.

Figure 3:
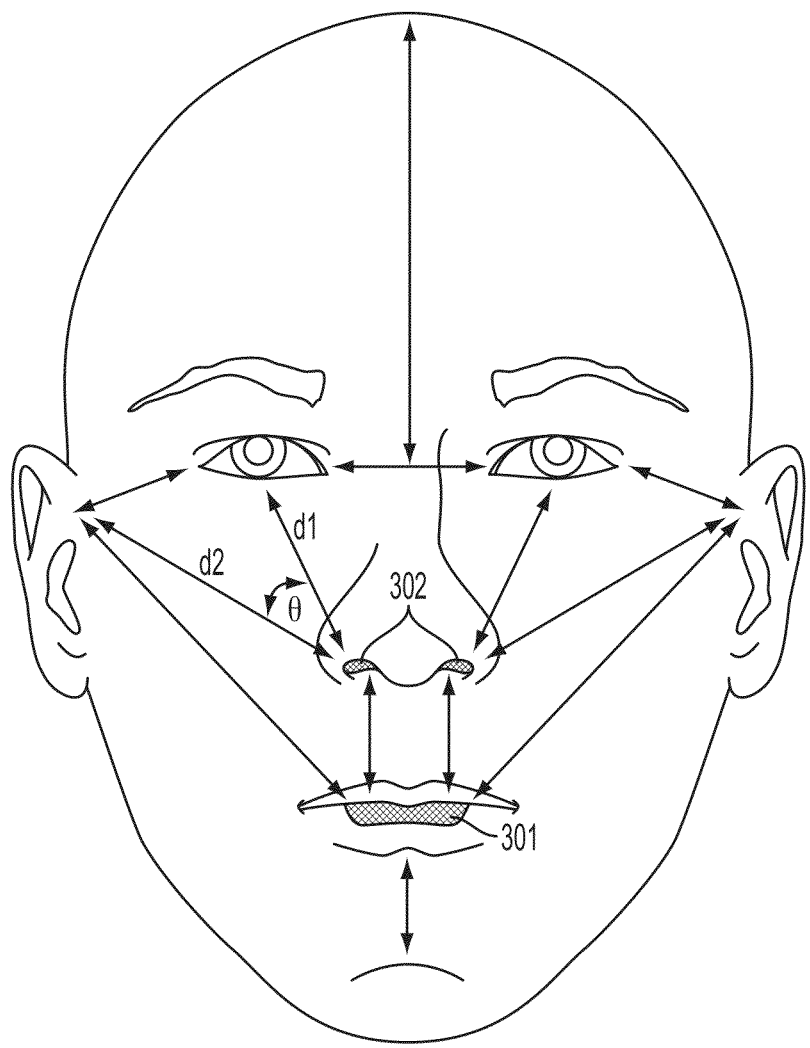
FIG. 3 is an illustration of a head and face showing a plurality of locational relationships (indicated by vectors and angles) associated with a human head which are used in accordance herewith to isolate the location of facial features associated with respiration, i.e., a nose and mouth.

A "locational relationship" refers to information about the location of a subject's extremities of the head and face which are used in accordance herewith to facilitate a determination of a location of the subject's facial features associated with respiration. Locational relationships can have many forms such as for example, vectors, angles, distances, formulas, text, images, and the like. For example, if the subject of interest is a person, facial features associated with respiration are their nose and mouth. The nose, for example, can be located in the thermal image by using the location of the eyes or relative to the location of the ears. The mouth can be located in the thermal image relative to the location of the ears and chin. Pre-defined locational relationships of facial features of different known subjects of interest are stored in a database. Example locational relationships which can be stored in a database as vectors and angles are shown in FIG. 3 are used to isolate the mouth 301 and nostrils, collectively at 302. Locational relationships are used herein to facilitate a determination of the location of the facial feature associated with respiration such that a respiration pattern can be determined.

A "respiration pattern" refers to the subject's breathing cycle tracked over time. The pattern of respiration is obtained by tracking pixel values of one or more facial features associated with respiration over time. Example respiration patterns are shown and discussed with respect to FIGS. 5A-B. The pattern usually shows periodic peaks and valleys associated with respiration cycles.

A "respiration rate" is the number of breathing cycles a subject takes within a certain amount of time (typically given in breaths/minute). Respiration rate is often measured when a subject is at rest and simply involves counting the number of breaths taking in a minute. During physical exertion when the body requires oxygenation at an increased rate, the respiration rate increases. Respiration rates may increase without physical activity due to fever, for example, or other medical conditions. The following chart shows average human respiration rates by age:

<1 Year: 30-40 breaths per minute
1-3 Years: 23-35 breaths per minute
3-6 Years: 20-30 breaths per minute
6-12 Years: 18-26 breaths per minute
12-17 Years: 12-20 breaths per minute
Over 18: 12-20 breaths per minute A "thermal image" or "thermal image video sequence" is an image or sequence of images captured using a thermal camera. Each thermal image comprises a plurality of pixels each corresponding to a surface temperature of a facial region across a thermal wavelength band. It should be understood that the teachings hereof are directed to image captured in the infrared wavelength range of: ≈7500 nm to ≈14,000 nm.

A "thermal camera" or "thermal image video system" is a camera system capable of capturing thermal images of a subject of interest. Specialized processors inside the thermal camera associate pixel color values with different temperatures and provide output RGB values of each pixel in the output image. The resolution for a thermal camera is effectively the size of the pixel. Smaller pixels mean that more pixels will go into the image giving the resulting image higher resolution and thus better definition. Because the amount of black-body radiation emitted by an object increases with the object's temperature, variations in temperatures of differing objects are observable in a thermal image. Thermal cameras generally consist of five primary components: 1) optics comprising specialized focal plane arrays (FPAs) that respond to defined wavelengths of the infrared range of the electromagnetic (EM) spectrum ($\approx 7.5$ to $\approx 14$ µm); 2) a detector for detecting radiation in the infrared range; 3) an amplifier for amplifying the received radiation; 4) a display for viewing the captured images; and 5) signal processing hardware such as: a CPU, memory, storage, for performing mathematical algorithms which interpret data and construct an IR image. Common thermal imaging systems are: InSb, InGaAs, HgCdTe, and QWIP FPA. Newer technologies utilize uncooled microbolometers as FPA sensors. The range of a thermal camera is approximately $-50°$ C. to $2000°$ C. Standard IR film is sensitive to a $250°$ C. to $500°$ C. variation. Thermal camera systems offer a relatively large dynamic range of temperature settings. However, for the purposes hereof, it is preferable that the camera's temperature range be relatively small $\approx 23.8°$ C. to $\approx 33.8°$ C., so that small temperature variations can be amplified in terms of pixel color changes. A smaller temperature range provides a better measure of temperature variation which, in turn, enables easier feature identification and location. Thermal camera systems are readily available in various streams of commerce. For example, the Inframetrics model 760 thermal camera has a dynamic range of $+/-2°$ C. to $+/-100°$ C. with the range corresponding to the 8-bit RGB values of R=G=B=0 and R=G=B=255). This camera is a long wave, scanner camera capable of storing images on a media. Thermal cameras are more expensive than their visible-spectrum counterparts and have a resolution which is lower than many commercially available optical cameras.

Example Flow Diagram

Figure 4:
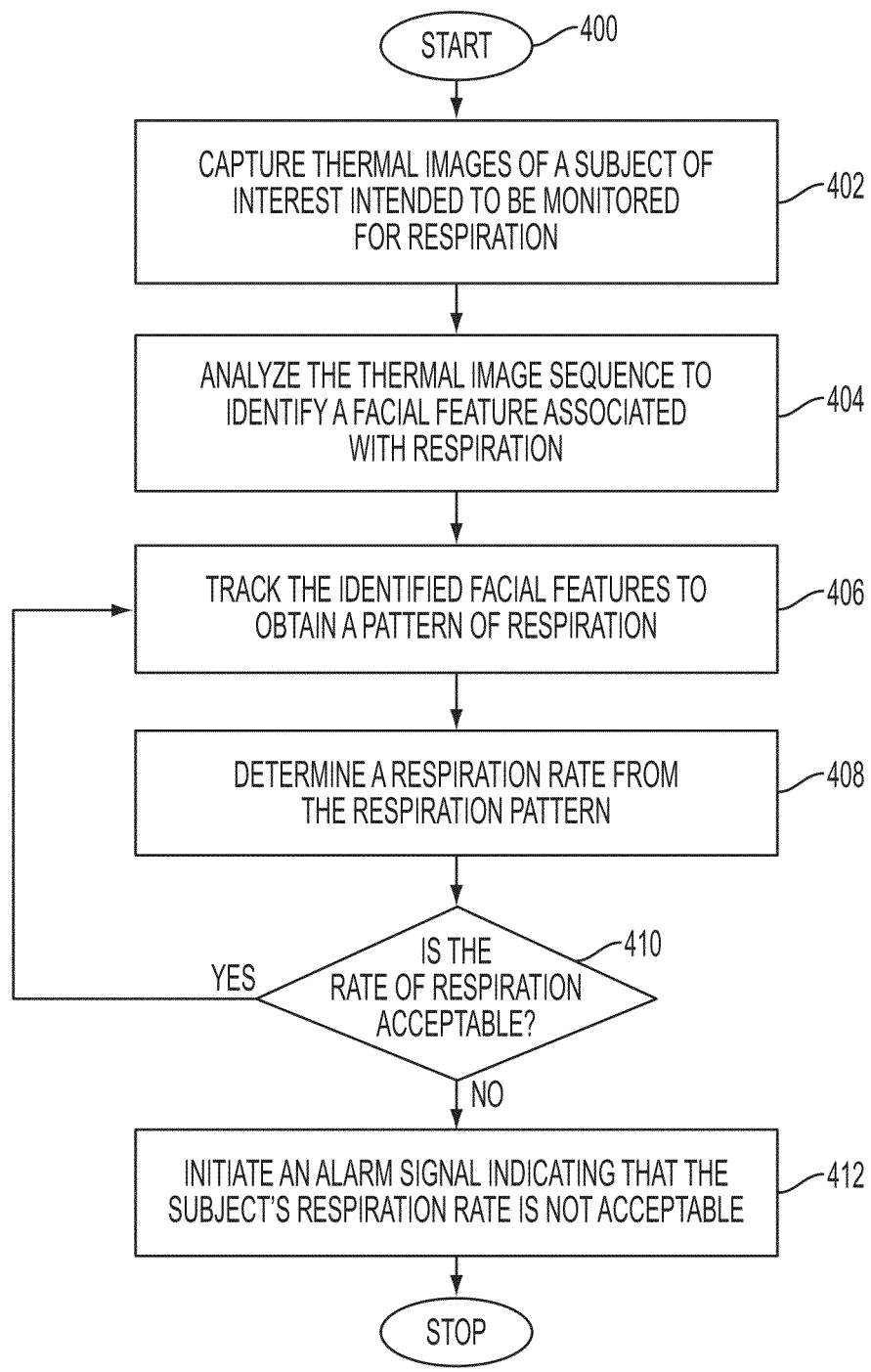
FIG. 4 is a flow diagram which illustrates one example embodiment of the present method for monitoring respiration using a thermal imaging system.

Reference is now being made to the flow diagram of FIG. 4 which illustrates one example embodiment of the present method for monitoring respiration using a thermal imaging system. Flow processing begins at 400 and immediately proceeds to step 402.

At step 402, thermal images of a subject of interest are captured using a thermal camera set to a temperature of a facial region of the subject. Each thermal image in the image sequence comprises a plurality of pixels with each pixel corresponding to a surface temperature of the facial region across the camera's thermal wavelength band. One example thermal image is shown in FIG. 2.

At step 404, the thermal images are analyzed to determine at least one facial feature associated with respiration. Analyzing the thermal images to determine the facial feature(s) associated with respiration involves identifying a location of at least one extremity of the subject's head and face. Once the locations of the extremities have been identified, the facial feature associated with respiration can be isolated in the thermal image relative to those location(s). In one embodiment, locational relationships are retrieved from a database and the location of the facial features associated with respiration is determined using the retrieved locational relationships. Once the facial features associated with respiration have been isolated in the thermal image, processing proceeds with respect to step 406.

Figure 5A:
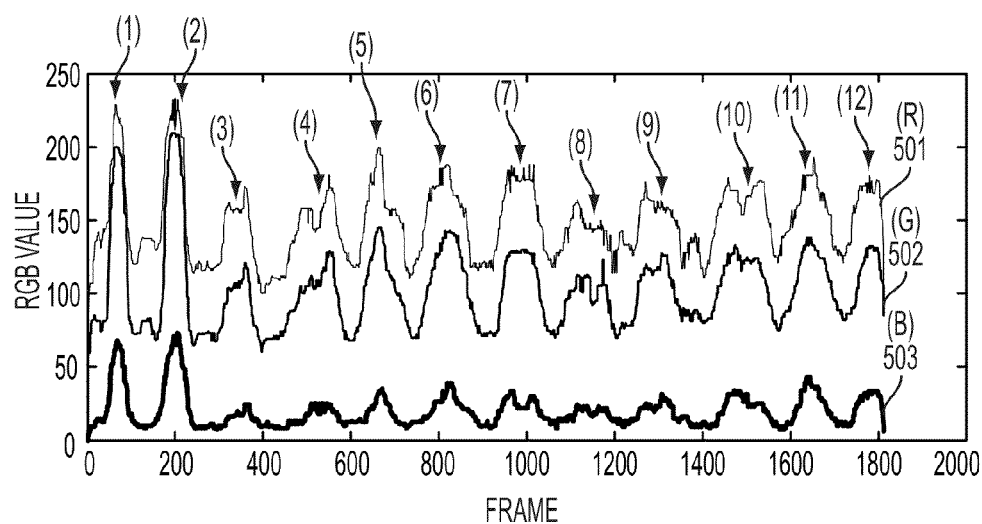
FIG. 5A shows a normal breathing pattern obtained by tracking R,G,B intensity values received from a thermal camera's R, G, and B channels, respectively.
Figure 5B:
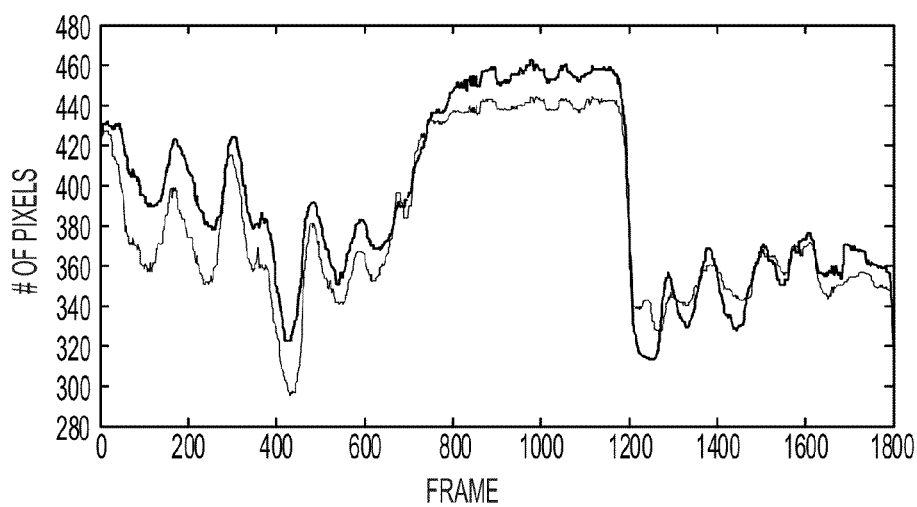
FIG. 5B shows an abnormal respiration pattern where the test subject was instructed to hold their breath for about 20 sec.

At step 406, the location of the subject's facial features associated with respiration is tracked over time to determine a pattern of respiration. In one embodiment hereof, identifying a pattern of respiration involves tracking some or all of the R, G, B, values obtained from the R, G, B, channels of the camera of pixels of image regions associated with the facial feature locations. An example plotted curves of normal and abnormal patterns of respiration are shown in FIGS. 5A and 5B, respectively. It should be appreciated that the R and G channels (501 and 502, respectively) are more useful than the B channel 503, as can be clearly seen in the curve of FIG. 5A, because exhaled air is warmer than the surface temperature of the face of the subject and R and G are associated with warmer temperatures in the thermal image by the camera's image processing system and B is associated with cooler temperatures. Another way is to covert the R, G, B values to temperature and track the temperature fluctuation during respiration.

Figure 6:
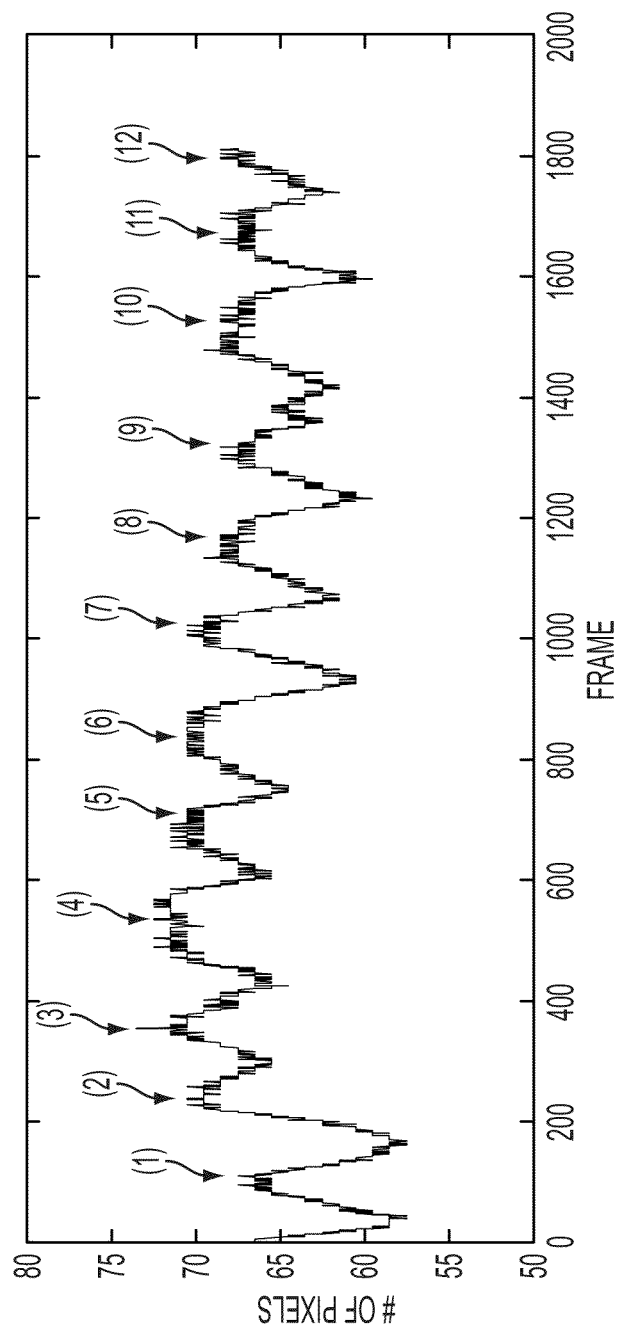
FIG. 6 shows an example of respiration being tracked by a movement of the subject's nasal area.

At step 408, a respiration rate is determined from the respiration pattern. Determining the respiration rate involves analyzing the plotted curve of R, G, B color values and counting the number of peaks over a pre-defined amount of time using methods such as Fourier transform or direct peak-valley detection algorithm. For example, from FIG. 5A, a total of 12 peaks can be counted in a 60 second window (filming at approximately 1800 frames/minute). As can be seen from the above-described Table, this correlates well to the number of breaths an adult subject would take in a minute and in the experiment, the rate was consistent with our visual counting of the number of inhales/exhales from the subject. In an alternative embodiment, respiration rate is determined by the motion of the nostrils, lips, or chest. FIG. 6 shows the respiration rate (12 breaths/minute) obtained by tracking the motion of the nostrils over a plurality of breathing cycles. This motion can be separated from other physical motion as movement in the image due to a respiratory function tends to be periodic at a certain frequency while other types of physical motion tends to be irregular. A visual comparison of the plots of FIGS. 5A and 6 show that, even though the phase is different, the number of peaks/valleys (breaths/minute) are approximately the same, using either technique.

At step 410, a determination is made whether the respiration rate falls outside a pre-defined threshold level. In one embodiment, this is effectuated by calculating a difference between the respiration rate and a pre-defined rate of respiration which can be retrieved from a storage device or memory. Alternatively, the pattern of respiration is compared to a pre-defined respiration pattern to determine a level of mismatch therebetween. If the determined respiration rate is acceptable, processing returns to step 406 wherein the identified facial features are continuously tracked to obtain a respiration pattern and a respiration rate is obtained from the ongoing respiration pattern in step 408. If the determined respiration rate is not within a pre-defined threshold level of acceptability, then processing continues with respect to step 412. In addition to check the respiration rate, the respiration pattern has to be closely monitored, e.g., the amplitude of the peaks/valleys and period of each cycle. For example, significantly reduced amplitude or the amplitude is below a threshold can indicate abnormal breathing patterns. Additionally, the respiration pattern from a certain time period can be compared with the subject's normal breath pattern retrieved from a database. Methods such as Dynamic Time Warping (DTW) or Longest Common Subsequence (LCSS) can be used to compare the time sequence.

At step 412, an alarm is initiated which indicates that the subject's respiration rate or respiration pattern is not acceptable. Initiating an alarm can be, for example, activating a light or audible noise, or otherwise producing a signal which activates a device which, in turns, performs an action or provides a notification. The kind of alarm signal being generated will depend on the particular embodiment wherein the teachings hereof are implemented. In this embodiment, once the alarm signal is activated, further processing stops. In another embodiment, processing repeats with respect to step 406 the subject's respiration pattern is continuously monitored despite the alarm. In various embodiments, a signal can be sent indicating delayed breathing or a change in heart rate. The present system can be used in conjunction with other health monitoring equipment or integrated therewith such that the initiated alarm signal causes these other device to perform intended functions. One example system for continuously processing the thermal images in accordance with the teachings hereof is described with respect to the block diagram of FIG. 7.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Block Diagram

Figure 7:
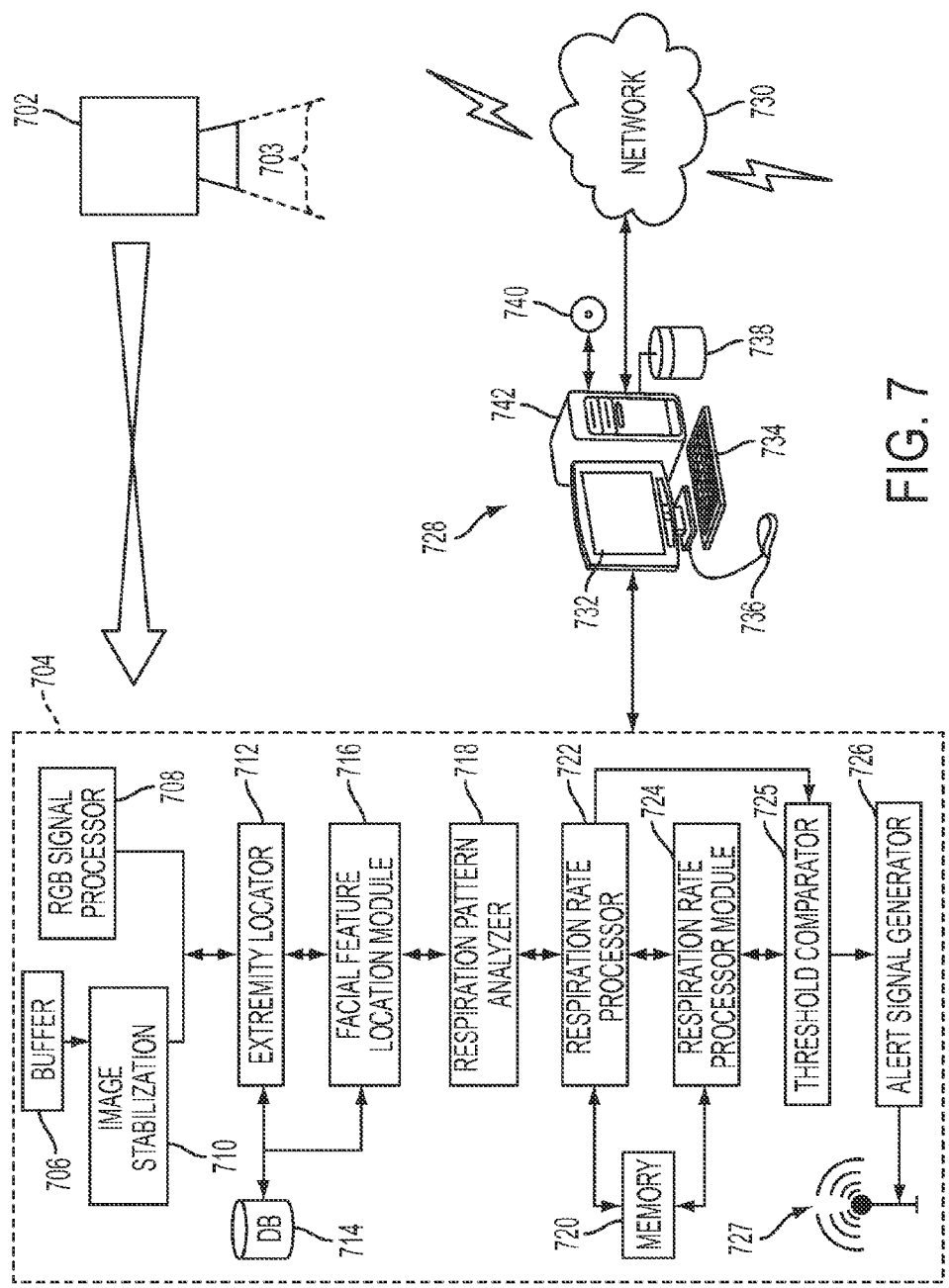
FIG. 7 is a block diagram of an example networked respiration monitoring system capable of implementing various aspects of the present method as described with respect to the flow diagram of FIG. 4.

Reference is now being made to FIG. 7 which is a block diagram of one example respiration monitoring system for implementing various aspects of the present method as described with respect to the flow diagram of FIG. 4.

In FIG. 7, thermal camera 702 captures a thermal image video sequence of a subject of interest whose head and face are in the camera's field of view 703. The captured video is continuously communicated to image processing system 704 along with R, G, B values obtained from the camera's RGB output channels. Image Processing System 704 is shown comprising a Buffer 706 for queuing the received thermal images for processing. Buffer 706 may further store data and mathematical formulas and representations as necessary to process the images according to various embodiments hereof. RGB Signal Processor 708 receives the RGB signals from respective RGB channels of thermal camera 702 and processes the pixel data to ensure that the pixel color values are within a predefined range and to associate pixels values with image areas within the frame. An Image Stabilizer 710 is provided for those systems where noise in the video sequence from either the motion of the camera or movement of the subject needs to be compensated for using, for example, image segmentation and point feature tracking. Such techniques are well known in the image processing arts. The thermal images and RGB values are provided to Extremity Locator Module 712 which identifies extremities of the subject's head and face. Facial Feature Location Module 716 receives the identified head and face extremities from Module 712 and locational relationships are retrieved from database 714 and used to determine a location of the subject's facial features associated with respiration. Respiration Pattern Generator 718 uses the RGB values associated with the location of the identified facial features and generates a respiration pattern which is stored to Memory 720. The generated respiration pattern is provided to Respiration Rate Processor 722 which determines the subject's rate of respiration by counting the number of peaks and valleys in the pattern over time. Respiration Rate Processor 722 is also in communication with Memory 720. The generated respiration rate and/or respiration pattern are provided to Threshold Comparator Module 725 which, in turn, determines whether the respiration rate or respiratory pattern is within acceptable parameters. Comparator 725 is in communication with Alert Signal Generator 726 which outputs a signal 727 if either the respiration rate or respiration pattern fall outside a pre-defined threshold level. Various portions of the captured IR image sequence and/or the RGB values obtained from camera 702 may be stored to Memory 720 and/or Storage Device 714 or may be communicated to Workstation 728 for storage or processing.

It should be appreciated that some or all of the functionality performed by any of the modules or processing units of system 704 can be performed, in whole or in part, by workstation 728 shown in communication with network 730 via a communications interface (not shown). In the embodiment of FIG. 7, workstation 728 is shown comprising a display monitor 732 for displaying information and for effectuating a user input or selection. Display 732 may be placed in communication with image processor system 704 and/or thermal video camera system 702 such that thermal images obtained by camera 702 can be viewed on the monitor display. A user or technician of the system of FIG. 7 may use the graphical user interface of workstation 728, e.g., keyboard 734 and mouse 736, to identify or select pixels, frames, images, and/or regions of interest for processing. These may be stored and/or retrieved from storage medium 738 or to computer readable media 740. Information stored to media 740 can be retrieved by a media reader such as, for example, a CD-ROM drive, located inside of computer case 742. Any of the modules and processing units of FIG. 7 can be placed in communication with database 738 and may store/retrieve therefrom data, variables, records, parameters, functions, machine readable/executable program instructions required to perform their intended functions. Moreover each of the modules of system 704 may be placed in communication with one or more devices over network 730.

It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network.

It is also contemplated that one or more aspects of the present method may be implemented on a dedicated computer system and may also be practiced in distributed computing environments where tasks are performed by remote devices that are linked through a network. The teachings hereof can be implemented in hardware or software using any known or later developed systems, structures, devices, and/or software by those skilled in the applicable art without undue experimentation from the functional description provided herein with a general knowledge of the relevant arts.

One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage media readable by a machine architecture or image processing system embodying executable program instructions capable of performing the methodology described in the flow diagrams. Additionally, the article of manufacture may be included as part of an operating system, a plug-in, or may be shipped, sold, leased, or otherwise provided separately, either alone or as part of an add-on, update, upgrade, or product suite.

It will be appreciated that various of the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for monitoring respiration using a thermal imaging system, the method comprising:
   capturing thermal images of a subject of interest intended to be monitored for respiration using a thermal image camera set to a temperature of a facial region of said subject, each thermal image comprising a plurality of pixels each corresponding to a surface temperature of said facial region across a thermal wavelength band;
   retrieving locational relationship of vectors and angles to determine said location of a facial feature consisting of a nose and a mouth by;
      using a location of eyes relative to a location of ears of said subject to locate said nose, and
      using a location of said ears and chin to locate said mouth;
   analyzing said thermal images to determine said location of said nose and said mouth;
   tracking physical motion of said facial feature over time to identify a physical motion pattern of respiration, said tracked physical motion being independent from determining a thermal pattern of respiration using thermal image analysis of said facial feature;
   determining a respiration rate from said physical motion pattern of respiration;
   performing any of: comparing said determined respiration rate to a pre-defined respiration rate, and comparing said determined physical motion pattern of respiration pattern to a pre-defined physical motion pattern of respiration pattern; and
   initiating an alarm in response to either of said comparisons falling outside a level of acceptability.

2. The method of claim 1, wherein analyzing said thermal images to determine said facial feature associated with respiration comprises:
   using pixel temperature values to identify a location of an extremity of the head and face of said subject of interest; and
   determining a location of said facial feature associated with respiration relative to said location of said identified head and face extremity.

3. The method of claim 2, wherein determining a location of said facial feature associated with respiration comprises:
   retrieving from a database at least one locational relationship associated with said identified extremity of said subject's head and face; and
   using said locational relationship to determine said location of said facial feature associated with respiration.

4. The method of claim 1, wherein identifying said pattern of respiration comprises tracking over time any of: R, G, and B, values of pixels associated with said facial feature associated with respiration obtained from the R,G,B, channels of said camera.

5. The method of claim 4, wherein determining said respiration rate comprises counting a number of peaks of said tracked pixel values over an amount of time.

6. The method of claim 1, wherein comparing said respiration rate to said pre-defined respiration rate comprises calculating a difference between said two respiration rates.

7. The method of claim 1, wherein comparing said determined physical motion pattern of respiration to said pre-defined physical motion pattern of respiration comprises determining a measure of mismatch between said two physical motion patterns of respiration.

8. The method of claim 1, further comprising compensating for a movement of said subject of interest in said captured video sequence by removing non-periodic motion of said facial feature.

9. The method of claim 1, wherein said alarm comprises any of: a visible light, an audible noise, and a signal which activates a device.

10. A system for monitoring respiration using a thermal imaging system, the system comprising:
   a thermal image camera set to a temperature of a facial region of a subject of interest intended to be monitored for respiration, said thermal camera capturing thermal images of said subject of interest, each thermal image comprising a plurality of pixels each corresponding to a surface temperature of said facial region across a thermal wavelength band;
   a memory and a storage medium; and
   a processor in communication with and said thermal image camera, said storage medium and said memory, said processor executing machine readable instructions for performing:
      retrieving locational relationship of vectors and angles to determine said location of a facial feature consisting of a nose and a mouth by;
         using a location of eyes relative to a location of ears of said subject to locate said nose, and
         using a location of said ears and chin to locate said mouth;
      analyzing said captured thermal images to determine said location of said nose and said mouth;
      tracking physical motion of said facial feature over time to identify a physical motion pattern of respiration, said tracked physical motion being independent from determining a thermal pattern of respiration using thermal image analysis of said facial feature;
      determining a respiration rate from said physical motion pattern of respiration;

performing any of: comparing said determined respiration rate to a pre-defined respiration rate, and comparing said determined physical motion pattern of respiration pattern to a pre-defined physical motion pattern of respiration pattern; and initiating an alarm in response to either of said comparisons falling outside a level of acceptability.

11. The system of claim 10, wherein analyzing said thermal images to determine said facial feature associated with respiration comprises:

using pixel temperature values to identify a location of an extremity of the head and face of said subject of interest; and determining a location of said facial feature associated with respiration relative to said location of said identified head and face extremity.

12. The system of claim 11, wherein determining a location of said facial feature associated with respiration comprises:

retrieving from a database at least one locational relationship associated with said identified extremity of said subject's head and face; and using said locational relationship to determine said location of said facial feature associated with respiration.

13. The system of claim 10, wherein identifying said pattern of respiration comprises tracking over time any of: R, G, and B, values of pixels associated with said facial feature associated with respiration obtained from the R,G,B, channels of said camera.

14. The system of claim 13, wherein determining said respiration rate comprises counting a number of peaks of said plotted pixel values over an amount of time.

15. The system of claim 10, wherein comparing said respiration rate to said pre-defined respiration rate comprises calculating a difference between said two respiration rates.

16. The system of claim 10, wherein comparing said determined physical motion pattern of respiration to said pre-defined physical motion pattern of respiration comprises determining a measure of mismatch between said two physical motion patterns of respiration.

17. The system of claim 10, further comprising compensating for a movement of said subject of interest in said captured video sequence by removing non-periodic motion of said facial feature.

18. The system of claim 10, wherein said alarm comprises any of: a visible light, an audible noise, and a signal which activates a device.

19. A computer implemented method for monitoring respiration using a thermal imaging system, the method comprising:

capturing thermal images of a subject of interest intended to be monitored for respiration using a thermal image camera set to a temperature of a facial region of said subject, each thermal image comprising a plurality of pixels each corresponding to a surface temperature of said facial region across a thermal wavelength band;

retrieving locational relationship of vectors and angles to determine said location of a facial feature consisting of a nose and a mouth by:

using a location of eyes relative to a location of ears of said subject to locate said nose, and using a location of said ears and chin to locate said mouth;

analyzing said thermal images to determine said location of said nose and said mouth;

tracking physical motion of said facial feature over time to identify a physical motion pattern of respiration, said tracked physical motion being independent from determining a thermal pattern of respiration using thermal image analysis of said facial feature;

determining a respiration rate from said physical motion pattern of respiration;

performing any of: comparing said determined respiration rate to a pre-defined respiration rate, and comparing said determined physical motion pattern of respiration pattern to a pre-defined physical motion pattern of respiration pattern; and initiating an alarm in response to either of said comparisons falling outside a level of acceptability.

20. The computer implemented method of claim 19, wherein analyzing said thermal images to determine said facial feature associated with respiration comprises:

using pixel temperature values to identify a location of an extremity of the head and face of said subject of interest; and determining a location of said facial feature associated with respiration relative to said location of said identified head and face extremity.

21. The computer implemented method of claim 20, wherein determining a location of said facial feature associated with respiration comprises:

retrieving from a database at least one locational relationship associated with said identified extremity of said subject's head and face; and using said locational relationship to determine said location of said facial feature associated with respiration.

22. The computer implemented method of claim 19, wherein identifying said pattern of respiration comprises:

tracking over time any of: R, G, and B, values of pixels associated with said facial feature associated with respiration obtained from the R,G,B, channels of said camera; and counting a number of peaks of said plotted pixel values over an amount of time.

23. The computer implemented method of claim 19, wherein comparing said respiration rate to said pre-defined respiration rate comprises calculating a difference between said two respiration rates.

24. The computer implemented method of claim 19, wherein comparing said determined physical motion pattern of respiration to said pre-defined physical motion pattern of respiration comprises determining a measure of mismatch between said two physical motion patterns of respiration.

25. The computer implemented method of claim 19, further comprising compensating for a movement of said subject of interest in said captured video sequence by removing non-periodic motion of said facial feature.

* * * * *